US00PP17660P2

(12) United States Plant Patent
Johnson, Jr.

(10) Patent No.: US PP17,660 P2
(45) Date of Patent: Apr. 24, 2007

(54) ***HYDRANGEA* PLANT NAMED 'LEMON DADDY'**

(50) Latin Name: *Hydrangea macrophylla*
Varietal Denomination: Lemon Daddy

(75) Inventor: Ozzie W. Johnson, Jr., Marietta, GA (US)

(73) Assignee: Itsaul Plants, Chamblee, GA (US)

( * ) Notice: Subject to any disclaimer, the term of this patent is extended or adjusted under 35 U.S.C. 154(b) by 0 days.

(21) Appl. No.: 11/293,770

(22) Filed: Dec. 2, 2005

(51) Int. Cl.
*A01H 5/00* (2006.01)

(52) U.S. Cl. ..... Plt./250
(58) Field of Classification Search ..... Plt./250
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Hydrangea* plant named 'Lemon Daddy', characterized by its compact and mounded growth habit; large and thick yellow green-colored leaves; and large inflorescences with light pink-colored flowers.

1 Drawing Sheet

Botanical designation: *Hydrangea macrophylla.*
Cultivar denomination: 'Lemon Daddy'.

BACKGROUND OF THE INVENTION

The present Invention relates to a new and distinct cultivar of *Hydrangea* plant, botanically known as *Hydrangea macrophylla,* and hereinafter referred to by the cultivar name Lemon Daddy.

The new *Hydrangea* originated from an open-pollination in May, 2000, of the *Hydrangea macrophylla* cultivar Big Daddy, disclosed in U.S. Plant Pat. No. 14,527, as the female, or seed, parent with an unknown selection of *Hydrangea macrophylla.* The cultivar Lemon Daddy was discovered and selected by the Inventor as a single plant within the progeny of the stated open-pollination in a controlled environment in Marietta, Ga. in April, 2001.

Asexual reproduction of the new cultivar by vegetative cuttings in Chamblee, Ga., since March, 2002, has shown that the unique features of this new *Hydrangea* are stable and reproduced true to type in successive generations.

SUMMARY OF THE INVENTION

Plants of the cultivar Lemon Daddy have not been observed under all possible environmental conditions. The phenotype may vary somewhat with variations in environment such as temperature and light intensity without, however, any variance in genotype.

The following traits have been repeatedly observed and are determined to be the unique characteristics of 'Lemon Daddy'. These characteristics in combination distinguish 'Lemon Daddy' as a new and distinct cultivar:

1. Compact and mounded growth habit.
2. Large and thick yellow green-colored leaves.
3. Large inflorescences with light pink-colored flowers.

Plants of the new *Hydrangea* can be compared to plants of the female parent, the cultivar Big Daddy. In side-by-side comparisons conducted in Chamblee, Ga., plants of the new *Hydrangea* differed from plants of the cultivar Big Daddy in the following characteristics:

1. Plants of the new *Hydrangea* were more compact than plants of the cultivar Big Daddy.
2. Plants of the new *Hydrangea* had smaller leaves than plants of the cultivar Big Daddy.
3. Plants of the new *Hydrangea* had yellow green-colored leaves whereas plants of the cultivar Big Daddy had green-colored leaves.
4. Plants of the new *Hydrangea* had smaller inflorescences than plants of the cultivar Big Daddy.

Plants of the new *Hydrangea* can also be compared to plants of the *Hydrangea macrophylla* cultivar Oganba, not patented. In side-by-side comparisons conducted in Chamblee, Ga., plants of the new *Hydrangea* differed from plants of the cultivar Oganba in the following characteristics:

1. Plants of the new *Hydrangea* were more vigorous than plants of the cultivar Oganba.
2. Plants of the new *Hydrangea* had larger leaves than plants of the cultivar Oganba.
3. Plants of the new *Hydrangea* had larger inflorescences than plants of the cultivar Oganba.

BRIEF DESCRIPTION OF THE PHOTOGRAPH

The accompanying colored photograph illustrates the unique appearance of the new cultivar, showing the colors as true as it is reasonably possible to obtain in colored reproductions of this type. Colors in the photograph may differ from the color values cited in the detailed botanical description which accurately describe the colors of the new *Hydrangea.* The photograph is a side perspective view of a typical plant of 'Lemon Daddy'.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photograph and in the following description were grown in Chamblee, Ga. in an outdoor nursery and under conditions which closely approximate commercial production conditions. Plants were about one year old when the photograph and description were taken. The photograph and description were taken during the summer.

Botanical classification: *Hydrangea macrophylla* cultivar Lemon Daddy.

Parentage:

*Female, or seed, parent.*—*Hydrangea macrophylla* cultivar Big Daddy, disclosed in U.S. Plant Pat. No. 14,527.

*Female, or seed, parent.*—Unknown selection of *Hydrangea macrophylla,* not patented.

Propagation:

*Type cutting.*—By vegetative cuttings.

*Time to initiate roots, summer and winter.*—About two weeks at 75° F.

*Time to produce a rooted cutting or liner, summer.*—About five weeks at 85° F.

*Time to produce a rooted cutting or liner, winter.*—About six weeks at 85° F.

*Root description.*—Fine, fibrous; white in color.

*Rooting habit.*—Freely branching.

Plant description:

*Form/growth habit.*—Compact and mounded plant habit; bushy perennial shrub.

*Plant height, soil level to top of plant plane.*—About 27 cm.

*Plant diameter or area of spread.*—About 33 cm.

*Branching habit.*—When pinched, freely branching with lateral branches potentially developing at every code.

*Lateral branches.*—Length: About 23 cm. Diameter: About 9 mm. Internode length: About 2.7 cm. Texture: New growth, smooth; mature, woody and without lenticels. Color: Developing stems: Close to 144A. Mature stems: Closest to between 199A and 199B.

*Foliage description.*—Leaves large and thick; simple, opposite and durable. Length: About 17 cm. Width: About 14 cm. Shape: Ovate. Apex: Acute. Base: Obtuse. Margin: Serrate. Texture, upper and lower surfaces: Smooth, glabrous. Venation pattern: Pinnate. Color: Developing and fully expanded foliage, upper surface: Close to 145A; under full sun conditions, color becoming closer to 150A. Developing and fully expanded foliage, lower surface: Close to 145B. Venation, upper surface: Close to 144A to 144B. Venation, lower surface: Close to 144B to 144D. Petiole: Length: About 4 cm. Diameter: About 7 mm. Texture, upper and lower surfaces: Smooth, glabrous. Color, upper and lower surfaces: Close to 144B.

Flower description:

*Flower type and habit.*—Single flowers arranged on terminal globular panicles with large showy sepals. Flowers persistent. Fragrance, not detected.

*Natural flowering season.*—Continuously flowering during the early summer in Chamblee, Ga.

*Flower longevity.*—Flowers last about four weeks on the plant.

*Quantity of flowers.*—Freely flowering; about 90 flowers per panicle.

*Panicle length.*—About 8.5 cm.

*Panicle diameter.*—About 15 cm.

*Flower diameter.*—About 3.6 cm.

*Flower depth* (*height*).—About 4 mm.

*Flower buds.*—Length: About 3 mm. Diameter: About 2 mm. Shape: Globulose. Color: Close to 144A.

*Petals.*—Arrangement: About four in a single whorl. Length: About 2.25 mm. Width: About 2 mm. Shape: Roughly ovate. Apex: Acute. Base: Attenuate. Margin: Entire. Texture, upper and lower surfaces: Smooth, glabrous. Color, upper and lower surfaces: Close to 144C.

*Sepals.*—Arrangement: About four in a single whorl. Length: About 1.8 cm. Width: About 1.9 cm. Shape: Broadly ovate. Apex: Rounded with acute tendencies. Base: Obtuse. Margin: Entire. Texture, upper and lower surfaces: Smooth, glabrous. Color: When opening, upper surface: Close to 63C. When opening, lower surface: Close to 63C to 63D. Fully opened, upper surface: 63C; color becoming closer to 144B with development. Fully opened, lower surface: 63C to 63D; color becoming closer to 145D with development.

*Peduncles.*—Angle: Upright. Strength: Moderately strong; flexible. Length: About 4.5 cm. Diameter: About 4 mm. Color: 144A to 144B.

*Pedicels.*—Angle: About 45° from vertical. Strength: Moderately strong; flexible and wiry. Length: About 2 cm. Diameter: About 1 mm. Color: Close to 63C.

*Reproductive organs.*—Stamens: Quantity per flower: About four or five. Anther shape: Oblong. Anther length: About 1 mm. Anther color: Close to 21A. Pollen amount: None observed. Pistils: Pistil quantity per flower: One. Pistil length: About 2 mm. Stigma shape: Two-lobed. Stigma color: Close to 145D. Style length: Less than 1 mm. Style color: Close to 145D. Ovary color: Close to 144B. Fruit/seed: Fruit and seed production has been observed.

Disease/pest resistance: Under commercial production conditions plants of the new *Hydrangea* have not been observed to be resistant to pathogens or pests common to *Hydrangea.*

Weather tolerance: Plants of the new *Hydrangea* have been shown to be tolerant to temperatures ranging from 6° F. to more than 95° F. Flowers of plants have exhibited excellent tolerance to wind and rain.

It is claimed:

1. A new and distinct cultivar of *Hydrangea* plant named 'Lemon Daddy', as illustrated and described.

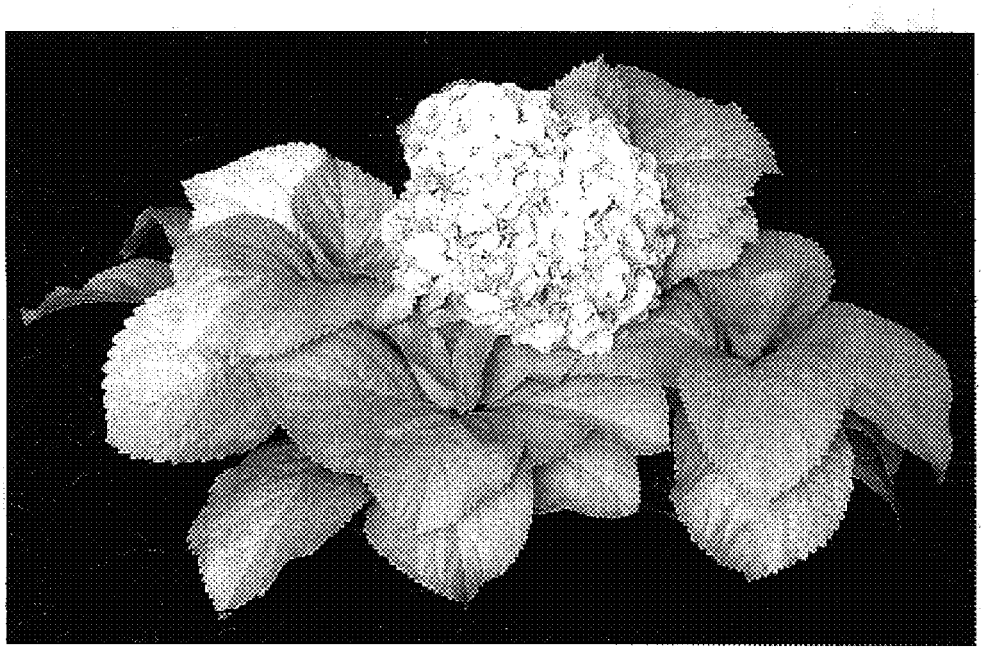

* * * * *